United States Patent [19]

Wetz et al.

[11] Patent Number: 5,741,221
[45] Date of Patent: Apr. 21, 1998

[54] KNEE-JOINT ORTHESIS HAVING DIFFERENT MEDICAL AND LATERAL HINGE MECHANISMS

[76] Inventors: Hans Henning Wetz, Weingartenstrasse 23, CH-8708 Männedorf; Hilaire Jacob, Gernstrasse 128, CH-8409 Winterthur, both of Switzerland

[21] Appl. No.: 541,451

[22] Filed: Oct. 10, 1995

[30] Foreign Application Priority Data

Oct. 7, 1994 [EP] European Pat. Off. ............. 94115801

[51] Int. Cl.⁶ .................................................. A61F 5/00
[52] U.S. Cl. ................................. 602/26; 602/16
[58] Field of Search ........................ 602/5, 16, 23, 602/26

[56] References Cited

U.S. PATENT DOCUMENTS

| | | | |
|---|---|---|---|
| 2,877,033 | 3/1959 | Koetke | 602/16 X |
| 4,241,730 | 12/1980 | Helfet | 602/26 |
| 4,256,097 | 3/1981 | Willis | 602/16 |
| 4,407,276 | 10/1983 | Bledsoe | 602/16 |
| 4,531,515 | 7/1985 | Rolfes | 602/16 |
| 4,628,916 | 12/1986 | Lerman et al. | 602/16 |
| 4,966,133 | 10/1990 | Kausek | 602/26 X |

FOREIGN PATENT DOCUMENTS 04720  4/1991  WIPO .................................. 602/16

*Primary Examiner*—Linda C. Dvorak
*Attorney, Agent, or Firm*—Laurence R. Brown

[57] ABSTRACT

In order to allow a knee-joint orthesis which is equipped with mounting structure for both the thigh and lower leg to take over the physiological movement of the knee-joint as precisely as possible, it is foreseen in accordance with the invention to connect the respective mounting structure pivotably by two intermediate rotation elements, whereby at least one rotation element includes a center of rotation which is displaceable relative to the mounting structures. The other rotation element includes preferably a center of rotation which is fixed relative to the mounting structures, and this rotation element is preferably arranged at the medial side of the knee-joint. Rotation elements with a displaceable center of rotation are designed preferably in form of a cross-over quadruple joint. The rotation element which possibly includes a fixed axis of rotation is formed preferably by a ball and socket joint. By this arrangement undesired influences of forces onto the knee-joint and the ligament apparatus of the knee-joint can be practically completely avoided.

3 Claims, 1 Drawing Sheet

KNEE-JOINT ORTHESIS HAVING DIFFERENT MEDICAL AND LATERAL HINGE MECHANISMS

BACKGROUND OF THE INVENTION

1. Field of the Invention

The present invention relates to a knee-joint orthesis having means for mounting the orthesis to the thigh and to the lower leg, which means are connected by rotation elements which are rotatable around a point of rotation.

2. Description of the Prior Art

When specifically the ligament apparatus of the human knee-joint is insured it is common procedure to prescribe a knee guiding orthesis. This orthesis shall take over to guide movements of the knee-joint as truly as possible, whereby unneeded and unnatural force influences onto the joint or ligament apparatus, resp., should be avoided as far as possible. The guiding of the movements shall allow a constant movement of the knee-joint, because immobilization of the joint during the course of healing of the ligaments is not desired.

A large problem at the fulfilling of this demand is that a bending of the knee is not a simple movement of a hinge joint, but is rather a complex course of movement having a axis of rotation which changes continuously with regard to the thigh and the lower leg.

A knee-joint orthesis is described for instance in EP 0 297 766. There, the knee-joint orthesis with mounting means for the thigh and the lower leg includes two identical rotation elements. These rotation elements are structured as a cross-over quadruple joint and form therewith joints with a variable axis of rotation. By this, the axis of rotation is indeed continuously displaced relative to the thigh and the lower leg when bending the orthesis, however, the alignment of the axis of the rotation relative to the thigh and lower leg, resp., remains always the same, thus only a parallel displacement of the axis occurs.

A specific embodiment of such a rotation element with a cross-over quadruple joint is described for instance in EP 0 546 330. It includes additional structure which prevents parts of the rotation element from rubbing at the knee.

SUMMARY OF THE INVENTION

Hence, it is a general object of the present invention to provide a knee-joint orthesis which is able to follow the course of the movement of the natural knee-joint in an improved manner and specifically which prevents as far as possible an additional influence of force onto the joint and accordingly onto the ligament apparatus during bending and stretching.

A further object is to provide a knee-joint orthesis in which at least one structure for mounting the orthesis to the thigh and to the lower leg includes a point of rotation which is displaceable relative to the mounting means.

Still a further object is to provide a knee-joint orthesis, which has two rotation elements which have a displaceable point of rotation, wherein two points of rotation feature a range of displacement which differ from each other.

In contrast to all known designs of knee-joint orthesis the invention does not use two identical or symmetrical rotation elements, but rather two rotation elements which differ from each other with regard to the geometry of the twisting. By this not only a parallel displacing of the axis of rotation of the knee-joint orthesis formed by the two points of rotation relative to the mounting means is achieved, but additionally also a change of the position of the axis of rotation such as occurs also when bending or stretching the human knee.

Yet a further object is to provide a knee-joint orthesis in which upon a pivoting of the orthesis one of two rotation elements features a fixed point of rotation relative to the mounting means and the other of the rotation relative to the mounting means and the other of the rotation elements features a displaceable point of rotation relative to the mounting means. Thus, at the one side of the knee-joint is provided a simple rotating element with a fixed point of rotation relative to the mounting means for the thigh and the lower leg, and at the other side a rotating element with a point of rotation which is variable relative to the mounting means is provided. It has been recognized that this simple design with only one complex structured rotation element follows the natural bending movement of the knee in such a precise manner that by such an inventive orthesis practically no forces occur which additionally act onto the knee and the ligament apparatus. The simple joint can for instance be a simple hinge joint.

Still a further object is to provide a knee-joint orthesis in which the rotation element which features the fixed point of rotation is located at the medial side of the knee which leads to a not parallel displacing of the axis of rotation of the orthesis such as occurs practically approximately in the same way also at the human knee. This location is also chosen when one rotation element has a smaller displaceable point of rotation.

A further object is to provide a knee-joint orthesis in which the fixed rotation element is a ball and socket joint. The use of a ball and socket joint prevents reliably a jamming of the point of rotation of the fixed rotation element when pivoting the orthesis.

Yet a further object is to provide a knee-joint orthesis in which the point of rotation of the rotation element having the displaceable point of rotation moves by about 15 mm upon a pivoting of the orthesis by 90°. It has been recognized that specifically a displacing of the point of rotation of the axis of rotation at the lateral (outer) side of the knee-joint by about 15 mm in the first about 20°–30° from the completely stretched position into a bent position avoids practically completely forces produced by the orthesis from acting onto the knee-joint. From a bending of about 40° from the completely stretched position up to a approximately rectangular bending of the knee-joint (thus about up to 90°) only a small, approximately parallel travel or displacement, resp., of the axis of rotation of the knee-joint relative to the mounting means for the thigh and for the lower leg occurs. By the inventive arrangement of the two different hinges at the medial and lateral side of the knee-joint this displacement of the instantaneous axis of rotation can be copied practically exactly. This leads advantageously to practically no additional influence of forces onto the knee-joint or the ligament apparatus caused by the movement of the orthesis.

A further object is to provide a knee-joint orthesis in which the rotation elements having a displaceable point of rotation are designed as a cross-over quadruple joint, i.e. where the mounting means are connected by two crossing link rods which are pivotably mounted to the mounting means. Such a joint can be realized in a simple manner and at low cost. The positions for the pivot points and the lengths of the two link rods can as is generally known be easily determined or set, resp., by the person skilled in the art in such a manner that the point of rotation of the instant axis of rotation displaces itself at this joint as desired.

Yet a further object is to provide a knee-joint in which the link joints are of an adjustable length which facilitates this task. This can be achieved for instance by threaded bars.

A further object is to provide a knee-joint orthesis in which the location of the rotation elements is adjustable relative to means for mounting the orthesis to the thigh and the lower leg. This allows the orthesis to be made to optimally suit the respective knee-joint of its bearer. This can proceed for instance in that the connection between the rotation elements and the mounting means is realized by a screwed joint which is displaceable within certain limits, for instance with sliding grooves or holes.

A further object is to provide a knee-joint orthesis which includes limiting elements for limiting the range of bending of the orthesis. By means of this overtaxing of the knee-joint and of the orthesis by undue movements can be avoided.

Still a further object is to provide a knee-joint orthesis in which structure for attaching the orthesis to the thigh and the lower leg have the shape of a shell or half shell. This gives an especially reliable and yet gentle fixing of the orthesis to the leg of the orthesis bearer. Such shapes can be produced either individually based on an imprint of the leg of the bearer of the orthesis or can be preshaped standard shapes equipped with adjustable inlets. Obviously also all other known mounting means such as for instance splints and webs may be used.

By the use of the knee-joint orthesis in accordance with the invention it becomes possible to achieve with regard to the joint and the ligament apparatus practically force-less guiding of the movement of the knee-joint over at least the most important range of bendin, from completely stretched up to at least bent rectangularly. With this, a substantial improvement of the course of healing of the ligament apparatus can be ensured without new or additional injuries being imposed thereon.

BRIEF DESCRIPTION OF THE DRAWINGS

The present invention will be better understood and objects other than those set forth above will become apparent when consideration is given to the following detailed description thereof when read in conjunction with the appended drawings, wherein:

FIG. 3 is a schematic perspective view of an orthesis structured in accordance with the invention; and FIG. 4 is a schematic of a further joint with a displaceable axis.

DETAILED DESCRIPTION OF THE PREFERRED EMBODIMENT

Figure 1:
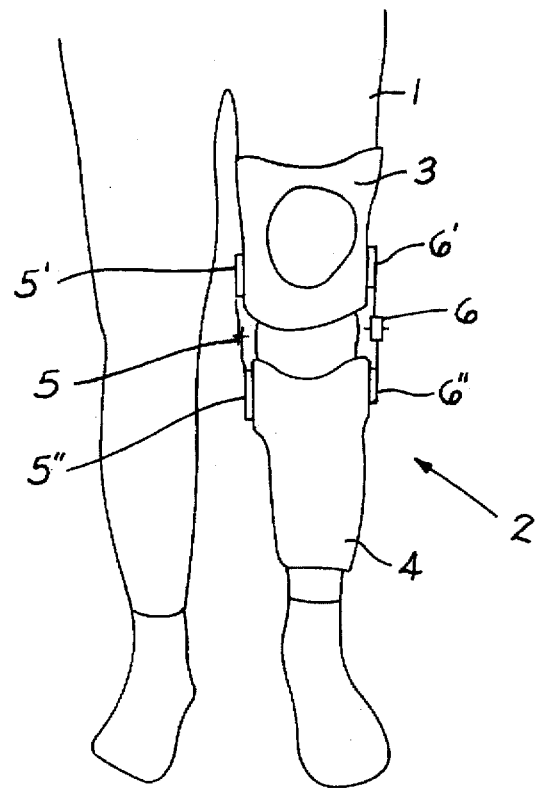
FIG. 1 is a schematic front view of an orthesis structured in accordance with the invention.

FIG. 1 illustrates the front view of the legs of a person with an orthesis 2 in accordance with the invention mounted to the left leg. The orthesis 2 consists of a structure 3 for mounting to the thigh and a structure 4 for mounting to the lower leg, which here are embodied for example in the shell design. The mounting structures 3 and 4 are interconnected by two rotation elements 5 and 6 in such a manner that during a bending of the leg 1 the bending movement of the knee is precisely guided by the orthesis. This is achieved in accordance with the invention in that the medial rotating element 5 is designed preferably as a simple joint, here for instance as a ball and socket joint. In contrast, the lateral joint 6 is designed as joint with a variable axis of rotation, for instance as cross-over quadruple joint.

In order to make the axes fo the rotation elements 5,6 to exactly suit the respective knee joint the rotating elements 5,6 are connected preferably by means of adjustable connecting pieces 5', 5" and 6', 6", resp. to the mount mean 3,4. This can be achieved for instance by screw connections through sliding holes as shown in FIG. 3.

Figure 2:
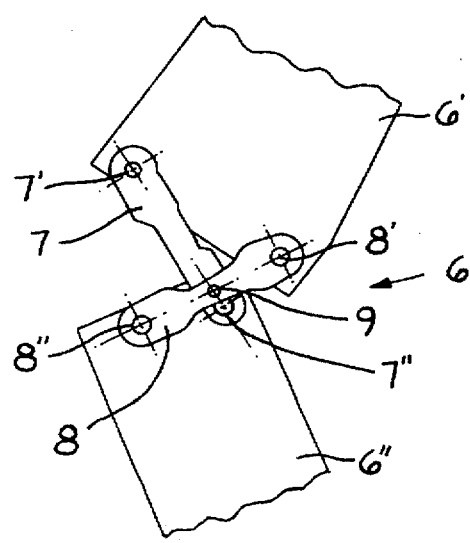
FIG. 2 is the schematic view of a joint with a displaceable axis.

In FIG. 2 the structure of the rotation element 6 is schematically and exemplary illustrated. The two connecting pieces 6' and 6" of the joint 6 are connected to each other by two crosswise guided connecting rods 7 and 8. Each of the two connecting rods 7,8 is mounted for rotation via joints 7', 7", 8', 8" and the length of the connecting rods 7 and 8, or can be set by a corresponding dimensioning of these values. Preferably, these values are dimensioned in such a manner, that the shifting of the center of rotation 9 through a range of rotation of about 90° (from the stretched knee to the rectangularly bent knee) amounts to about 15 mm.

By this design of the two rotation elements 5 and 6 a shifting of the momentaneous axis of rotation of the orthesis is arrived at which corresponds substantially to the actual shifting of the axis of rotation of the knee-joint. This leads advantageously to the fact that undesired influences of force onto the knee joint and the ligament apparatus can be substantially avoided by the movement of the orthesis. In order to ensure that this movement does not lead to a canting of the simple joint 5 this joint is preferably designed as ball and socket joint.

It has been found that when adjusting the orthesis 2 to the knee 1 the connection pieces 5',5" and 6',6" should be attached intially loose, i.e. easily moveable to the mounting means 3 and 4. Preferably these connections are shiftable for instance by use of sliding holes such as mentioned above. Thereafter the knee is bent once from the completely stretched position to a approximately rectangular position and only thereafter the connecting pieces 5',5" and 6',6", resp. are connected unmoveably to the mounting means 3 and 4.

As has been found by measurements, the forces acting onto the knee joint could be practically completely avoided by such an orthesis in accordance with the invention, in contrast to a symmetric use of two similar joints such as previously have been common practice.

Furthermore, at the same time preferably a simplification of the mechanics of such a knee orthesis is arrived at in that only one single relatively complicated and intrinsically structued joint with a displaceable axis must be used whereas the other joint is designed as a simple and thus also a low cost joint.

While there has been shown and described a presently preferred embodiment of the invention, it shall distinctly be understood that same is not limited thereto but may be variously embodied and practiced within the scope of the following claims.

We claim:

1. A knee-joint orthesis comprising in combination, mounting means for mounting the orthesis respectively to the thigh and to the lower leg, a pair or respective rotation elements for rotatively coupling the respective thigh and lower leg mounting means located respectively on medial and lateral knee sides of the orthesis, wherein one of said pair of rotation elements comprises a cross-over quadruple joint mechanism producing a movable point of rotation displaceable relative to the mounting means as the knee-joint is bent, and the other one of said pair of rotation elements comprises a simple rotary joint having a fixed axis of rotation as the knee-joint is bent located on the medial knee side of the orthesis.

2. The knee-joint orthesis of claim 1, in which the point of rotation of the rotation element having the displaceable point of rotation moves by about 15 mm upon a pivoting of the knee-joint by about the first 20° to 30° of a 90° knee-bend.

3. A knee-joint orthesis comprising in combination, mounting means for mounting the orthesis respectively to the thigh and to the lower leg, a pair or respective rotation elements for rotatively coupling the respective thigh and lower leg mounting means located respectively on medial and lateral knee sides of the orthesis, wherein one of said pair of rotation elements comprises a cross-over quadruple joint mechanism producing a movable point of rotation displaceable relative to the mounting means as the knee-joint is bent, and the other one of said pair of rotation elements comprises a simple rotary joint having a fixed axis of rotation as the knee-joint is bent located on the medial knee side of the orthesis, wherein the rotation elements with the displaceable point of rotation comprises a cross-over quadruple joint with two cross-link rods of an adjustable length which are pivotably mounted to the mounting means respectively at the thigh and lower leg.

* * * * *